United States Patent [19]
Smirnov et al.

[11] 4,214,584
[45] Jul. 29, 1980

[54] DEVICE FOR ADMINISTERING MEDICINAL PREPARATIONS

[76] Inventors: Boris A. Smirnov, ulitsa Borisa Galushkina, 17, kv. 28; Vyacheslav N. Mochalov, prospekt Mira, 122, kv. 174, both of Moscow; Valery P. Busygin, Krasnogorsk, Zheleznodorozhny proezd, 13, kv. 25, Moskovskaya oblast; Rustam I. Utyamyshev, prospekt Mira, 118, kv. 222, Moscow; Alexei I. Semenov, ulitsa Mira, 26, kv. 53, Klin, all of U.S.S.R.

[21] Appl. No.: 2,702
[22] Filed: Jan. 10, 1979

[30] Foreign Application Priority Data
Jan. 11, 1978 [SU] U.S.S.R. .................. 2567610

[51] Int. Cl.² .................................................. A61M 5/00
[52] U.S. Cl. ......................... 128/218 M; 128/272.1
[58] Field of Search ............... 128/215, 216, 218 R, 128/218 F, 218 M, 272.1, DIG. 28

[56] References Cited
U.S. PATENT DOCUMENTS

| | | | |
|---|---|---|---|
| 2,390,246 | 12/1945 | Folkman | 128/218 M |
| 3,810,469 | 5/1974 | Hurschman | 128/218 M |
| 3,946,732 | 3/1976 | Hurschman | 128/218 M |
| 3,977,402 | 8/1976 | Pike | 128/215 |

*Primary Examiner*—John D. Yasko
*Attorney, Agent, or Firm*—Burgess, Ryan and Wayne

[57] ABSTRACT

The device for administering medicinal preparations comprises an isolated capsule subdivided into a chamber for a first medicinal preparation and a chamber for a second medicinal preparation. Coaxially inside said isolated capsule concentrically therewith is the piston which bounds said chamber for the first medicinal preparation. Made fast on said piston is the injection needle having the hole located at the base of said piston. Provision is made in the device for a mechanical actuator of said piston, which is a spring-opposed pushrod located inside the housing which also accommodates the retaining member for said spring-opposed pushrod. Said chamber for the second medicinal preparation is arranged concentrically with said chamber for the first medicinal preparation so as to embrace the latter. Said isolated capsule is mounted traversably inside said housing, while communication between both of said chambers is established upon a positive extension of said isolated capsule from said housing outwards.

2 Claims, 4 Drawing Figures

DEVICE FOR ADMINISTERING MEDICINAL PREPARATIONS

The present invention relates to medical equipment and has particular reference to a device for administering medicinal preparations.

The present invention can be most advantageously used for mixing two or more medicinal preparations immediately prior to administration, one of said preparations being in a liquid state, while the other one or more preparations can be either a powder or a liquid, and for subsequent subcutaneous injection of the thus-obtained dispersions or solutions.

The device enables one to keep stored separately under sterile conditions, the medical preparations intended to be mixed before being injected, and thus administer freshly prepared solutions and mixtures.

One prior-type device for administering medicinal preparations (cf., e.g., U.S. Pat. No. 4,055,177 cl.128/218 published Oct. 10, 1977) is known in the present-state of the art to comprise a tube (capsule) confined from below by a diaphragm and subdivided, by means of a separator and the holder of an injection needle, into two chambers A and B, a needle unit and a piston, whereonto a rod is screwed.

Upon pressing the rod, the separator is displaced under the action of the liquid contained in the chamber A. On the point of the injection needle ruptures the separator. Thus, the liquid is free to pass through the hollow injection needle into the chamber B containing a liquid or solid component. Once the entire bulk of the liquid has been conveyed to the chamber B, one must remove the cap from the injection needle whose inner end breaks the diaphragm under the action of a spring.

The abovesaid known device for administering medicinal preparations is inconvenient and hardly applicable for carrying out autoinjecting, during which the sterility of the needle may be violated. Furthermore, getting the device ready for operation is rather complicated as it involves the removal of a protective cap from the injection needle. In addition, a certain amount of air is present in the tube (capsule) of the device, contained between the chambers A and B, the ingress of said air into the tissues during injecting the medicinal preparation is inadmissible.

It is a primary object of the present invention to provide a device for administering medicinal preparations which would be capable of preparing various quality and different concentration medicinal preparations immediately before their administration, depending upon the original components, so as to extend the functional capacities of the device.

It is another object of the present invention to provide and facilitate self-injecting and preserve the sterility of the injection needle.

The essence of the present invention resides in a device for administering medicinal preparations, comprising an isolated capsule subdivided into a chamber for a first medicinal preparation and a chamber for a second medicinal preparation; a piston accommodated in the isolated capsule coaxially therewith to set bounds to the chamber for the first medicinal preparation; an injection needle made fast on the piston; a mechanical actuator of the piston fashioned as a spring-opposed pushrod located in a housing, wherein provision is made for a retaining member of the spring-opposed pushrod. According to the invention, the chamber for the second medicinal preparation is arranged concentrically with the chamber for the first medicinal preparation so as to embrace the latter, and the isolated capsule is mounted traversably inside the housing, whereas communication between the both of the chambers is established upon a positive extension of the isolated capsule from the housing outwards, and the injection needle has a hole located at the base thereof.

Such a construction of the device for administering medicinal preparations enables one to keep the medical preparations stored separately in the isolated capsule under sterile conditions before their being mixed, and to mix said preparations prior to administration. It also renders self-injection possible in a semiautomatic mode of operation due to releasing the retaining member of the spring-opposed pushrod. In addition, the injection needle remains sterile under any manipulation of the device.

To extend the functional capacities of the device for administering medicinal preparations, the chamber for the second medicinal preparation is subdivided, by virtue of partitions, into compartments the number of which corresponds to a required quantitative composition of the medicinal preparations or their concentration.

In the following description, the invention is illustrated in a detailed description of an exemplary embodiment thereof given with reference to the accompanyng drawings, wherein.

Figure 1:
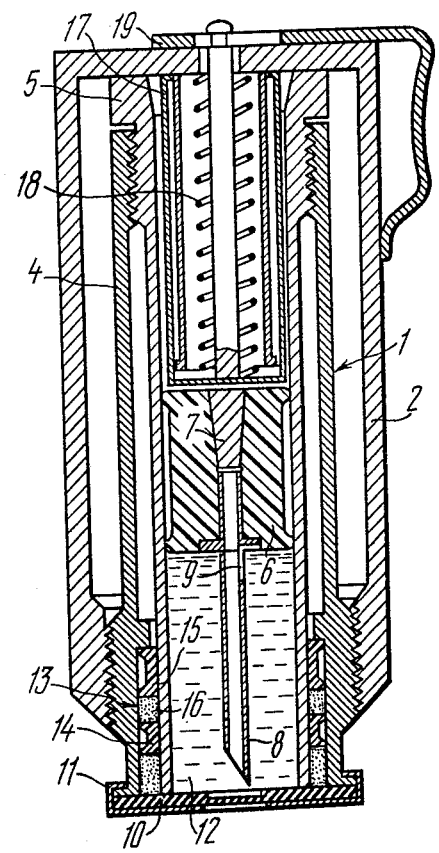
FIG. 1 is a schematic view of a device for administering medicinal preparations in an assembled state, according to the invention.
Figure 2:
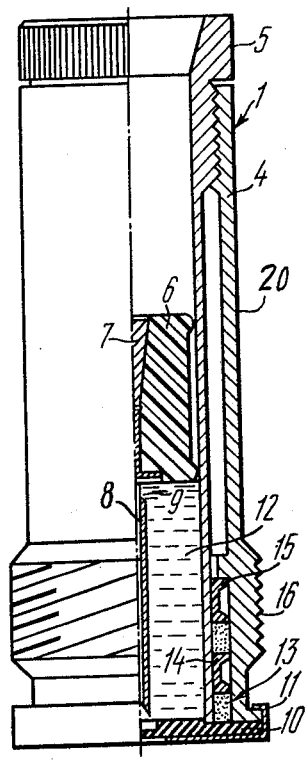
FIG. 2 is a charged isolated capsule, according to the invention.

The herein-proposed device for administering medicinal preparations comprises an isolated capsule 1 (FIG. 1) traversably accommodated in a housing 2. The isolated capsule 1 (FIGS. 1, 2) has an outside shell 4 provided with an external thread 16 on one of its end and with an internal thread 20 on the other end thereof. The outside shell 4 accommodates a cylindrical inside shell 5 provided with an external thread which engages thread 20. The isolated capsule 1 accommodates a piston 6 coaxial with and slidably movable within said capsule, said piston having a taper plug 7 and an injection needle 8 which is provided with a hole 9 located at the base of the piston 6.

The outside shell 4 is hermetically sealed at one end by a diaphragm 10 which is held against the flange of the outside shell 4 by virtue of cover 11. The piston 6 bounds a chamber 12 for a first medicinal preparation. A second chamber 13 for a second medicinal preparation is formed between outside shell 4 and the inside shell 5 of the isolated capsule 1, is concentric with the chamber 12, and embraces the latter. The chamber 13 for the second medicinal preparation is subdivided by partitions 14 and 15 into a number of spaces 16 to suit the required quantitative composition of the medicinal preparations or the concentration thereof.

Figure 3:
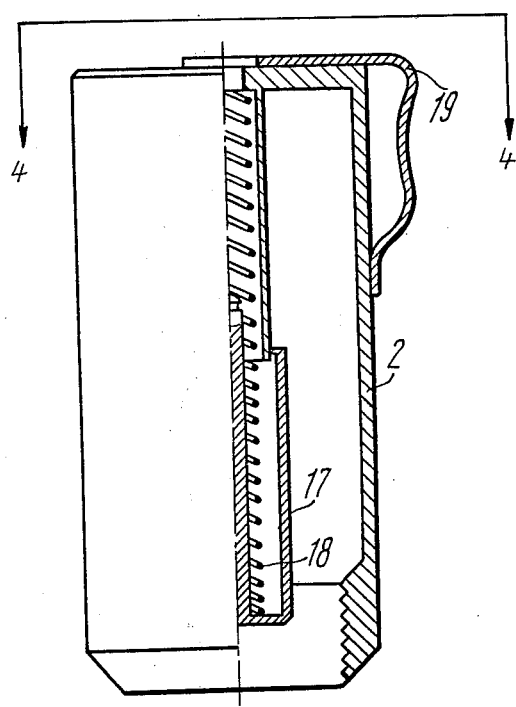
FIG. 3 is a piston mechanical actuator in a released state, according to the invention.
Figure 4:
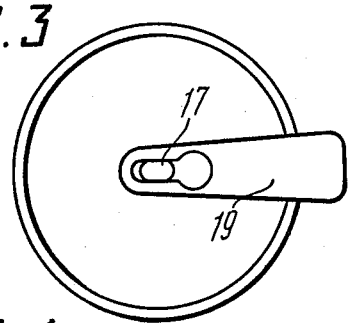
FIG. 4 is a top view of FIG. 3 taken along 4—4 in said FIG. 3.

The mechanical actuator of the piston 6 is made as a pushrod 17 (FIG. 3) which accommodates a spring 18. The mechanical actuator of the piston 6 (FIG. 2) has a retaining member 19 (FIGS. 3, 4) for the spring-opposed pushrod 17.

The device operates as follows.

For charging the device with the medicinal preparation, the inside shell 5 (FIG. 1) of the isolated capsule 1 is rotated counterclockwise along its thread to move upwards, thus untightening the chamber 12 for the first medicinal preparation on the side of the diaphragm 10. Then the inside shell 5 is raised to the level of the partition 14 or 15 depending upon a preselected amount of the component contained in the chamber 13 for the second medicinal preparation. Upon preparing the required medicine (a mixture or solution), the inside shell 5 of the isolated capsule 1 is rotated clockwise to return it to the initial position. Then the spring 18 is set up by the pushrod 17 and locked with the retaining member 19, whereupon the isolated capsule 1 containing the thus-prepared medicinal preparation is placed into the housing 2 of the mechanical actuator of the piston 6, wherein the capsule is held in position by virtue of the thread provided on the outside shell 4.

Next, the device is approached to the body portion selected for a self-injection, and the retaining member 19 is pressed to carry out the self-injection. Pressing upon the retaining member 19 causes the spring 18 to actuate the pushrod 17 which, while cooperating with the piston 6, imparts a translational motion thereto. As a result, the injection needle 8 which is made fast on the piston 6, pierces the diaphragm 10 and is introduced into the body muscular tissue. The medicinal preparation prepared in the chamber 12 is injected through the hole 9 in the needle 8 located at the base of the piston 6.

Once the entire amount of the prepared medicinal mixture has been injected into the tissue, the isolated capsule 1 is removed, the pushrod 17 is returned to the initial position by virtue of compressing the spring 18 and locked in position by the retaining member 19.

The device is then ready to receive a fresh isolated capsule.

What is claimed is:

1. A device for administering medicinal preparations, comprising:

a housing;

an isolated capsule movably mounted inside said housing;

a piston movably mounted inside and coaxially with said isolated capsule and providing one wall of the chamber for a first medicinal preparation accommodated within said isolated capsule;

an injection needle made fast on said piston and having a hole located at the base of the piston;

a chamber for a second medicinal preparation accommodated in said isolated capsule and arranged concentrically to said chamber for the first medicinal preparation and embracing the latter, both of said chambers getting inter-communicated upon a positive extension of said isolated capsule from said housing outwards;

a mechanical actuator of said piston made as a spring-opposed pushrod and located in said housing;

a retaining member for said spring-opposed pushrod, provided in said housing.

2. A device for administering medicinal preparations, comprising:

a housing;

an isolated capsule movably mounted inside said housing;

a piston movably mounted inside said isolated capsule coaxially therewith and traversably therealong so as to bound the chamber for a first medicinal preparation accommodated within said isolated capsule;

an injection needle made fast on said piston and having a hole located at the base of the piston;

a chamber for a second medicinal preparation accommodated in said isolated capsule and arranged concentrically to said chamber for the first medicinal preparation and embracing the latter, both of said chambers getting intercommunicated upon a positive extension of said isolated capsule from said housing outwards;

partitions subdividing said chamber for the second medicinal preparation into a number of spaces to suit a required quantitative composition of medicinal preparations;

a mechanical actuator of said piston made as a spring-opposed pushrod and located in said housing;

a retaining member for said spring-opposed pushrod, provided in said housing.

* * * * *